United States Patent
Meinert et al.

(10) Patent No.: US 8,029,977 B2
(45) Date of Patent: Oct. 4, 2011

(54) METHOD FOR PRESERVING ORGANS OR LIMBS USING A COMPOSITION CONTAINING A SILOXANE AND A SEMIFLUORINATED ALKANE AND/OR HYDROFLUOROETHER

(75) Inventors: Hasso Meinert, Neu-Ulm (DE); Bernhard Günther, Dossenheim (DE); Wilfried Hiebl, Illertissen (DE); Bastian Mühling, Erbach (DE); Daniel Brandhorst, Linden (DE)

(73) Assignee: NOVALIQ GmbH, Heidelberg (DE)

( * ) Notice: Subject to any disclaimer, the term of this patent is extended or adjusted under 35 U.S.C. 154(b) by 623 days.

(21) Appl. No.: 12/094,951

(22) PCT Filed: Nov. 23, 2006

(86) PCT No.: PCT/EP2006/011247
§ 371 (c)(1),
(2), (4) Date: Oct. 3, 2008

(87) PCT Pub. No.: WO2007/059968
PCT Pub. Date: May 31, 2007

(65) Prior Publication Data
US 2009/0226875 A1     Sep. 10, 2009

(30) Foreign Application Priority Data
Nov. 23, 2005  (DE) .......................... 10 2005 055 811

(51) Int. Cl.
*A01N 1/00*     (2006.01)

(52) U.S. Cl. .......................................... 435/1.1; 435/1.2
(58) Field of Classification Search ....................... None
See application file for complete search history.

(56) References Cited

U.S. PATENT DOCUMENTS

| 6,274,303 | B1 | 8/2001 | Wowk et al. |
| 2002/0128527 | A1 | 9/2002 | Meinert |
| 2003/0022148 | A1 | 1/2003 | Seki |

FOREIGN PATENT DOCUMENTS

| EP | 0 440 925 | 12/1990 |
| WO | WO 93/01798 | 2/1993 |
| WO | WO 93/16974 | 9/1993 |
| WO | WO 97/12858 | 4/1997 |
| WO | WO 97/12852 | 10/1997 |

OTHER PUBLICATIONS

Matsumoto et al. "Perfluorocarbon for Organ Preservation before Transplantation." *Transplantation*. vol. 74, No. 12. 2002. pp. 1804-1809.

Voiglio et al. "Aerobic Perservation of Organs Using a New Perflubron/Lecthin Emulsion Stablized by Molecular Dowels." *Journal of Surgical Research*. vol. 63. 1996. pp. 439-446.

Hartert et al. "Effects of Perfluorocarbon emulsions on cultured human endothelial cells." *Art. Cells, Blood Subs., And Immob. Biotech.* vol. 25. No. 6. 1997. pp. 563-575.

*Beilsteins Manual of Organic Chemistry*. vol. 4, Part 2, pp. 1879 (1963).

*Primary Examiner* — Sandra Saucier
(74) *Attorney, Agent, or Firm* — Merchant & Gould P.C.

(57) ABSTRACT

Use of a composition which contains at least one semifluorinated alkane compound and at least one liquid siloxane, wherein the composition is of a density in a range of 0.8 to 1.5 g/cm$^3$, for preserving organs or limbs.

23 Claims, No Drawings

METHOD FOR PRESERVING ORGANS OR LIMBS USING A COMPOSITION CONTAINING A SILOXANE AND A SEMIFLUORINATED ALKANE AND/OR HYDROFLUOROETHER

BACKGROUND OF THE INVENTION

The invention concerns the use of a composition for preserving organs and limbs.

When organs or limbs are removed for a transplant they have to be stored until they are used in such a way that they suffer as little damage and spoiling as possible. Limbs which were severed and which are to be sewn back on again must be stored in a protected condition until they are integrated into the blood circulation again. The organs or limbs have to be protected from mechanical damage but also from harmful effects which occur by virtue of the fact that they are not integrated into the blood circulation. In order to retard the degradation process or the onset of decay which occurs as soon as the organs or limbs are separated from the circulatory system, various methods have been developed. One possible option involves storing the organs or limbs in liquid perfluorocarbons. Perfluorocarbons have the advantage that they are inert, that is to say they do not react with the organ tissue. Perfluorocarbons also have the advantage that they have a high absorption capability for oxygen so that when they are stored in perfluorocarbons the organs or limbs can be supplied with oxygen. That prolongs the survival time of the organ or the limbs. Use of the perfluorocarbons was an important advance in transplant medicine.

A disadvantage when using perfluorocarbons however is that they are of a very high density which is far above the density of the organs or limbs. For that reason the organs or limbs float up in the liquid instead of being immersed therein. In order to provide that the organ is enclosed by perfluorocarbons it is necessary to apply a force for counteracting the buoyancy. In general that is done by the organs or limbs being held under the surface of the perfluorocarbons with holding devices. It is only then that it is ensured that they are adequately supplied with oxygen and do not come into contact with the environment which is harmful to organs or limbs. However capillary systems in the tissue can be mechanically damaged by the holding devices. The damage to the structures may be so extensive that a transplant or sewing back on is no longer a possibility.

A further disadvantage of perfluorocarbons is their low dissolving power for other compounds. It is therefore not possible to add to a preserving solution of perfluorocarbons, active substances which can perform a function that is helpful in terms of preserving the organs and limbs.

It is known for organs to be stored at very low temperature, that is to say to effect cryopreservation. It will be noted however that for that purpose water first has to be removed from the tissue so that the cells do not burst during the freezing process. Storage is effected in the case of cryopreservation at temperatures in the range of $-100°$ C. to $-180°$ C. Cryopreservation is suitable for cells which are not very sensitive to mechanical stresses, but it leads to major problems in relation to organs and delicate tissues.

The demands on a composition for preserving organs or limbs are thus many and varied.

SUMMARY OF THE INVENTION

Therefore the object of the Invention is to provide a composition with which organs and limbs can be stored and preserved in a careful fashion in such a way that they suffer as little damage as possible.

A further object is to provide a sterile composition which is immediately ready for use, which does not require dehydration of the tissue and which can be adapted to the prevailing conditions in a simple fashion.

A further object of the invention is to provide a composition which makes it possible to dissolve substances in order to stabilise organs and limbs and to avoid harmful influences.

It was surprisingly found that a composition which contains at least one semifluorinated alkane compound which is liquid at ambient temperature and which can be a semifluorinated alkane and/or a hydrofluoroether, and at least one siloxane which is liquid at ambient temperature, affords a possible way of carefully storing organs and limbs, wherein they can be supplied with oxygen at the same time as semifluorinated alkane compounds and liquid siloxanes afford a good gas dissolving power. In addition the composition according to the invention provides the possibility of adding substances which further improve the preservation of organs and limbs.

In addition the composition according to the invention offers the advantage that it forms a barrier layer around the organ or the limbs to be preserved, and that prevents contamination of the organs or limbs to be stored. The composition itself is per se hostile to germs and can be well sterilised.

The compositions according to the invention are chemically, physically and physiologically inert and non-toxic.

The subject-matter of the invention is therefore the use of a composition which contains at least one liquid semifluorinated alkane compound, at least one liquid siloxane or a combination of at least one liquid semifluorinated alkane compound and at least one liquid siloxane and is of a density in a range of 0.8 to 1.5 g/cm$^3$, for preserving organs and limbs.

Semifluorinated alkane compounds are amphiphilic compounds with lipophobic R$_F$-segments and lipophilic R$_H$-segments. Both semifluorinated alkanes and also hydrofluoroethers are understood as semifluorinated alkane compounds according to the Invention. The compounds are made up of blocks of perfluorinated alkanes (R$_F$) and blocks of non-fluorinated alkanes (R$_H$). The perfluorinated and non-fluorinated blocks can be joined either by a bond (semifluorinated alkanes) or by way of an oxygen atom (hydrofluoroethers). In accordance with the invention both compounds in which fluorinated and non-fluorinated blocks alternate and also compounds in which a fluorinated block is joined to a non-fluorinated block are considered. In particular semifluorinated alkanes as are described in WO 97/12858 are suitable. It is possible to use both di-block compounds R$_F$-A-R$_H$ and also tri-block compounds R$_F$-A-R$_H$-A-R$_F$, wherein A respectively independently signifies a bond or oxygen. Preferably di-block compounds are used. In that case the blocks may respectively have both straight and branched components. The unbranched and semifluorinated alkane compounds are of the formulae:

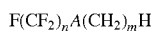

with $n = 1 - 20$ $m = 3 - 20$ wherein A is a bond or oxygen.

The branched semifluorinated alkane compounds can also have within the perfluoroalkyl groups FCH-units
with X=CF$_3$, C$_2$F$_5$, C$_3$F$_7$ or C$_4$F$_9$ and also within the alkyl groups HCY-units
with Y=$CH_3$, $C_2H_5$, $C_3H_7$, or $C_4H_9$.

A —$CX_2$-group can also be contained within a perfluoroalkyl chain and a —$CY_2$-group may also be contained within an alkyl chain.

Instead of the perfluoroalkyl group $F_3C$— an $FCX_2$— or $F_2CX$-group
with X=$C_2F_5$, $C_3F_7$ or $C_4F_9$
can also be bound in the molecule at the end and equally instead of the alkyl group $H_3C$— an $HCY_2$— or $H_2CY$-group
with Y=$C_2H_5$, $C_3H_7$ or $C_4H_9$
can also be bound in the molecule at the end.

If however in the case of all specified isomers, that is to say straight or branched semifluorinated alkanes, the total number of carbon atoms in the perfluoroalkyl portion always remains as previously stated in the limits of n=1-20, the number of carbon atoms in the alkyl part also remains in the predetermined limits of m=3-20. In a preferred embodiment semifluorinated alkanes are used, In which n is of a value of 3 to 10 and m is of a value of 3 to 12.

The semifluorinated alkanes used according to the invention are liquid at ambient temperature. Very short-chain compounds which are gaseous at ambient temperature cannot be considered for a use for a composition according to the invention. Preferably semifluorinated alkanes are used, whose melting temperature is higher than −50° C.

DETAILED DESCRIPTION OF THE PREFERRED EMBODIMENT(S)

In a preferred embodiment the semifluorinated alkane compounds are used in highly purified form. For that purpose it is possible to use the process described in WO 93/16974 whereby the semifluorinated alkane compounds are firstly treated with acid permanganate solution and thereafter autoclaved or heated under reflux with a mixture of aqueous potassium hydroxide solution (4-8 n), CaO or BaO and a nucleophilic agent (for example a secondary amine) at 150 to 180° C. for a prolonged period. The reaction product is then separated from the aqueous alkaline phase which possibly still contains alcohol and the amine phase, treated several times in succession with dilute mineral acid, $NaHCO_3$ solution, distilled water, water-free $Na_2SO_4$ and water-free $CaCl_2$ and subjected to fractional distillation over a powerful column. The semifluorinated alkanes treated in that way, in accordance with IR-, $^1$H-NMR-, $^{19}$F-NMR- and GC/MS-spectroscopy, are free from groupings which with intramolecular HF-elimination can lead to the formation of toxic olefinic by-products.

The process described in WO 93/16974 can be used for the quantitative determination of groupings which can lead to intramolecular HF-separation or the exchange of a fluorine atom bound to the carbon by means of a nucleophilic agent, with which process ionisable fluoride is detected in the reaction of the sample material with hexamethylene diamine in nonane or decane by heating for several hours at 120 to 150° C., wherein any liberated fluoride is detected by means of an ion-sensitive electrode. After the purification process, fluoride ions should be detectable at the highest up to a proportion of 40 ppm, wherein the detection limit for the fluoride concentration is less than or equal to $10^{-5}$ mol $l^{-1}$.

As stated above in accordance with the invention both semifluorinated alkanes and also hydrofluoroethers as well as a combination of both can be used as the semifluorinated alkane compounds. The respectively appropriate compounds or combinations can be selected by the man skilled in the art. Thus it is possible to use a semifluorinated alkane compound or a combination of two or more semifluorinated alkane compounds, wherein both combinations of various semifluorinated alkanes and also combination of various hydrofluoroethers as well as combinations of at least semifluorinated alkane and at least one hydrofluoroether are suitable. As semifluorinated alkane compounds have a high gas dissolving power that class of compounds can be used alone for preserving the tissue but only on the condition that its density is in the claimed range. If semifluorinated alkane compounds whose density lies outside the claimed range are to be used, a preferred embodiment involves the use of a combination with at least one liquid siloxane.

In accordance with the present invention the expression liquid siloxanes which can also be referred to as silicone oils is used to denote in particular those compounds which are made up of dialkyl siloxane units and/or diaryl siloxane units and are capable of flow at ambient temperature and body temperature. The alkyl residues are straight-chain or branched and have up to six carbon atoms. The preferred alkyl residues are methyl residues. Preferably phenyl residues are used as the aryl residues. They are chemically, physically and physiologically inert, that is to say they react neither with constituents of the tissue with which they come into contact, that is to say proteins, lipids, etc, nor with further constituents present in the composition such as semifluorinated alkanes or further additives.

The siloxanes used are preferably those which are practically not or only very slightly cross-linked. Siloxanes are commercially available in many different variants and the man skilled in the art can easily select that which is of optimum suitability for the respective purpose. Low-viscosity mixtures of siloxanes which are commercially available are particularly suitable. Preferably the silanes used are those which are of a viscosity in the range of 0.5 to 1000 mPas, preferably 0.5 to 500 mPas, wherein the viscosity is respectively measured with a falling ball viscosimeter at ambient temperature.

Preferably a combination of at least one semifluorinated alkane compound and at least one siloxane is used for the composition according to the invention. In that case the components are mixed in such proportions that the density of the finished composition is in the desired range. The components—semifluorinated alkane compound and siloxane—are normally miscible with each other in any ratio at ambient temperature and any ratio of those components is therefore suitable.

The composition according to the invention remains homogeneous over a period of at least a year, sterile and physically-chemically stable and does not suffer separation of the mixture upon storage at ambient temperature (20 to 25° C.).

The density of the composition can be adjusted by altering the proportions of the components and depends on the organ to be stored therein or the respective limbs. Preferably the density is selected in dependence on the respective organ or the respective limbs to be preserved. If a higher level of oxygen demand is wanted then the proportion of semifluorinated alkane compounds is increased or only semifluorinated alkane compounds are used. If the oxygen demand can be less or a density in the lower range is desired the proportion of siloxane is increased or pure siloxane is used.

The density is preferably set in dependence on the organ and is appropriately in a range of 0.8 to 1.5, preferably at 0.9 to 1.3 and particularly preferably 1.01 to 1.25 g/cm$^3$.

Preferably the density of the composition is so adjusted that the organ or the limbs are immersed in the medium without using a holding device and are preferably completely submerged and in particular preferably float in a suspended condition in the medium without sinking down and without floating up. Storage in a floating condition suspended in the composition is storage which is most careful for the tissue and avoids any mechanical damage. So that the composition according to the invention can act as a barrier layer preferably the organ or the limbs should be completely submerged.

The composition used according to the invention is distinguished by its high gas dissolving power and makes it possible to provide oxygen for the tissue to be stored or preserved. The proportion of dissolved oxygen is preferably so set as to ensure a sufficient supply of oxygen. The oxygen content is preferably set in dependence on the organ, that is to say depending on the respective oxygen demand of the respective tissue to be preserved. In a preferred embodiment the composition has 3-50% by volume, preferably 10-40% by volume of oxygen at ambient temperature and alternatively oxygen saturation.

By virtue of its amphiphilic structure, the lipophillc and the lipophobic components, it is possible to dissolve substances which are insoluble in semifluorinated alkanes, in semifluorinated alkane compounds. That also affords the possibility of providing dissolved in the composition compounds which make it possible to improve the preserving of tissues. Thus for example it is possible to add active substances such as antibiotics, steroids, anti-inflammatories, cytostatics or additives which protect and stabilise the composition such as antioxidants. The semifluorinated alkane compounds serve in that respect as solution aids so that substances which are not soluble in siloxanes alone can also be added in mixtures of semifluorinated alkane compounds and siloxanes. Examples that can be mentioned are 5-fluorouracil, daunomycin, ibuprofen, N-acetylcysteine, carotenolds, retinol palmitate and α-tocopherol.

Nutrients for organs and tissue can also be added to the composition used according to the invention in order to provide for optimum supply for the organ during transport. If the active substances and nutrients used do not dissolve in the composition according to the invention then in a further embodiment it is possible to use co-solvents which dissolve the active substance or nutrient and are dissolved in the composition according to the invention of semifluorinated alkane compound and siloxane. Co-solvents which are suitable in that connection are for example alcohols such as monovalent and polyvalent alcohols with 1 to 6 C-atoms, for example ethanol, n-propyl alcohol, isopropyl alcohol, butanol, glycerine, sorbitol etc. Further compounds suitable as co-solvents are ethers and esters. Water is not considered in this connection, the composition used according to the invention is water-free.

If a composition according to the invention is used, which either comprises a combination of semifluorinated alkane compound and siloxane or siloxane alone, it is recommended that the more highly viscous adhering components of the preserving fluid are washed off the tissue prior to the further use thereof, that is to say in the transplant or being sewn on. For that purpose the use of preferably high-purity semifluorinated alkane compounds is particularly advantageous by virtue of the compatibility thereof with siloxanes. It is recommended that absorbed or adsorbed components of the preserving liquid be washed off the respective tissue or eluted.

In accordance with the invention therefore a composition is used which makes it possible for tissue and in particular organs or limbs to be stored and preserved in a careful fashion without mechanical impairment while at the same time ensuring the oxygen supply thereto. The use according to the invention can take place at ambient temperature and requires neither dehydration of the organs or limbs nor storage at very low temperature. The composition according to the invention is biologically and physiologically compatible and maintains the quality and safeguards the life of the isolated organ or limbs.

The composition used according to the invention is produced in per se known manner by the respective proportions being mixed together. Preferably the individual components are mixed in sterile form and processed under sterile conditions. The resulting composition is homogeneous and physically-chemically stable at ambient temperature.

Siloxanes have a good gas dissolving power even if somewhat lower than semifluorinated alkane compounds. Preferably siloxanes of a density in the range of 0.75 to 0.98 g/cm$^3$ are used for the mixing operation.

The composition according to the invention is produced for carefully storing organs and tissue. As the composition is highly stable and can be stored over a long period, for example over a period of at least a year at an ambient temperature of 15 to 42° C., it is very well suited to being kept in readiness for emergency situations. Thus a composition according to the invention can be carried for example in ambulances in order to receive limbs which have to be transported after an accident, without involving major complication or expenditure.

Examples which are intended to further explain the subject-matter of the present invention without thereby limiting it are set forth hereinafter.

Example 1

Previously sterilised silicone oil 1000 and previously sterilised perfluorohexyloctane are mixed in a KGW Isotherm vessel with an IKA stirrer at ambient temperature under sterile conditions. The ratio of silicone oil 1000 to F6H8 is 69.5:30.5 (w/w). Then oxygen is introduced into the solution at ambient temperature under sterile conditions at a flow rate of 2000 ml/min until an oxygen content of 30% by volume is reached. The density of the solution obtained is 1.05 g/cm$^3$. If there is a wish to provide a composition of lower density the proportion of silicone oil 1000 is increased. If the wish is to increase density the proportion of perfluorohexyloctane can be increased.

Example 2

Previously sterilised silicone oil 50 is saturated with oxygen by oxygen being introduced under sterile conditions at ambient temperature at a flow rate of about 5000 ml/min until complete oxygen saturation is reached. The silicone oil 50 enriched with oxygen can then be used for the storage of tissue.

Example 3

Previously sterilised silicone oil 100 and previously sterilised perfluorobutylhexane are mixed in a KGW Isotherm vessel with an IKA stirrer under sterile conditions at ambient temperature. The desired viscosity and/or density can be set by way of the mixing ratio of silicone oil 100 to F4H6. Oxygen enrichment of the solution (flow rate 3000 ml/min) to 15% by volume is then effected by introducing oxygen at ambient temperature under sterile conditions.

Example 4

Previously sterilised perfluorohexyloctane and previously sterilised α-tocopherol are mixed in the KGW Isotherm vessel with an IKA stirrer under sterile conditions at ambient temperature. The ratio of F6H8 to α-tocopherol is 98:2 (w/w). Oxygen is then introduced into the solution under sterile conditions at ambient temperature at a flow rate of 1000 ml/min until the solution has an oxygen content of 8% by volume.

Example 5

Previously sterilised ethylnonafluorobutylether and previously sterilised silicone oil 3 are mixed in the KGW Isotherm vessel with an IKA stirrer under sterile conditions at ambient temperature. The desired viscosity and/or density can be adjusted by way of the mixing ratio of silicone oil 3 to ethylnonafluorobutylether. Oxygen is then introduced into the solution at ambient temperature under sterile conditions at a flow rate of 1500 ml/min oxygen until an oxygen content of 25% by volume is reached.

The invention claimed is:

1. A method of preserving an isolated organ or a limb comprising contacting the organ or limb with a water-free composition comprising at least one semifluorinated alkane or hydrofluoroether and at least one siloxane, wherein the composition has a density of 0.8 to 1.5 g/cm$^3$, and wherein the semifluorinated alkane or hydrofluoroether and siloxane are liquid at ambient temperature, thereby preserving the organ or limb.

2. The method according to claim 1, wherein the semifluorinated alkane or hydrofluoroether has the formula $R_F A R_H$ where $R_F$ is a straight or branched perfluoroalkyl group with 1-20 C atoms, $R_H$ is a straight or branched saturated alkyl group with 3-20 C atoms and A is a carbon to carbon bond or oxygen atom.

3. The method according to claim 2, wherein the at least one semifluorinated alkane or hydrofluoroether has branched units within the $R_F$ group and/or within the $R_H$ group.

4. The method according to claim 3, wherein the at least one semifluorinated alkane or hydrofluoroether can contain one or more branches designated X in the RF group, where X is $CF_3$, $C_2F_5$, $C_3F_7$ or $C_4F_9$ and can contain one or more side chains designated Y in the RH group, where Y is $CH_3$, $C_2H_5$, $C_3H_7$ or $C_4H_9$.

5. The method according to claim 2, wherein the semifluorinated alkane or hydrofluoroether RF is a straight or branched perfluoroalkyl group with 3-10 C atoms and RH is a straight or branched saturated alkyl group with 3-12 C atoms.

6. The method according to claim 1, wherein the composition contains a mixture of semifluorinated alkanes, a mixture of hydrofluoroethers or a combination of a least one semifluorinated alkane and at least one hydrofluoroether.

7. The method according to claim 1, wherein the siloxane is a dialkysiloxane and/or a diarylsiloxane, wherein the alkyl residues in the dialkylsiloxane can be straight-chain or branched and have 1-6 carbon atoms.

8. The method according to claim 1, wherein the siloxane is of a viscosity of 0.5 to 1000 mPas.

9. The method according to claim 8 wherein the siloxane is of a viscosity in the range of 0.5 to 500 mPas.

10. The method according to claim 1, wherein the siloxane is a polydimethylsiloxane or a mixture of polydimethylsiloxanes.

11. The method according to claim 1, wherein the composition has an oxygen content which corresponds to the oxygen demand of the organ or limbs to be preserved.

12. The method according to claim 1, wherein the composition further contains 10 to 40% by volume of oxygen, measured at ambient temperature.

13. The method according to claim 1, wherein the composition is saturated with oxygen at ambient temperature.

14. The method according to claim 1, wherein the composition additionally includes one or more active substances and/or nutrients.

15. The method according to claim 14, wherein the active substance or nutrient is an antibiotic, steroid, anti-inflammatory, cytostatic, virustatic and/or stabilizing agent.

16. The method according to claim 14, wherein the active substance or nutrient is 5-fluorouracil, daunomycin, aciclovir, ganciclovir, ibuprofen, N-acetylcysteine, carotenoids, retinol palmitate and/or α-tocopherol.

17. The method according to claim 14, wherein the active substance or nutrient is a vitamin, lipid-bearing substance and/or easily decomposable fat and/or oil.

18. The method according to claim 14, wherein the composition further comprises a co-solvent for the active substance and/or nutrient.

19. The method according to claim 1, wherein the composition additionally contains at least one anti-oxidant.

20. The method according to claim 19 wherein the anti-oxidant is retinol palmitate and or α-tocopherol.

21. The method according to claim 1, wherein the density of the composition is 0.9 to 1.3 g/cm$^3$.

22. The method according to claim 1, wherein the density of the composition is 1.01 to 1.25 g/cm$^3$.

23. A method of preserving an isolated organ or a limb comprising contacting the organ or limb with a water-free composition consisting essentially of at least one semifluorinated alkane or hydrofluoroether and at least one siloxane, wherein the composition has a density of 0.8 to 1.5 g/cm$^3$, and wherein the semifluorinated alkane or hydrofluoroether and siloxane are liquid at ambient temperature, thereby preserving the organ or limb.

* * * * *